(12) United States Patent
Sudhir et al.

(10) Patent No.: US 8,840,678 B2
(45) Date of Patent: Sep. 23, 2014

(54) DRUG-ELUTING BIOABSORBABLE RENAL ARTERY STENT FOR RENAL CANCER AND INFLAMMATORY DISORDERS

(75) Inventors: Krishnankutty Sudhir, Santa Clara, CA (US); Joanne M. Ferguson, Mont Albert (AU)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 84 days.

(21) Appl. No.: 13/371,210

(22) Filed: Feb. 10, 2012

(65) Prior Publication Data

US 2013/0211490 A1 Aug. 15, 2013

(51) Int. Cl.
*A61F 2/84* (2006.01)

(52) U.S. Cl.
USPC ..................... 623/23.65; 623/1.11

(58) Field of Classification Search
USPC ............... 623/1.11, 1.21, 1.26, 23.64, 23.65; 606/200, 151; 424/422
See application file for complete search history.

(56) References Cited

U.S. PATENT DOCUMENTS

| | | | | |
|---|---|---|---|---|
| 8,062,677 | B2 * | 11/2011 | Komorowski | 424/655 |
| 2007/0283552 | A1 | 12/2007 | Gale et al. | |
| 2008/0091262 | A1 * | 4/2008 | Gale et al. | 623/1.38 |
| 2008/0124373 | A1 * | 5/2008 | Xiao et al. | 424/423 |
| 2008/0275537 | A1 | 11/2008 | Limon | |
| 2008/0300573 | A1 * | 12/2008 | Consigny et al. | 604/509 |
| 2010/0004735 | A1 | 1/2010 | Yang et al. | |
| 2011/0190875 | A1 * | 8/2011 | Gale et al. | 623/1.42 |
| 2011/0251677 | A1 * | 10/2011 | Pacetti | 623/1.42 |
| 2011/0319976 | A1 * | 12/2011 | Iyer et al. | 623/1.11 |
| 2012/0203202 | A1 * | 8/2012 | Consigny et al. | 604/508 |
| 2012/0303112 | A1 * | 11/2012 | Armstrong et al. | 623/1.16 |
| 2012/0330405 | A1 * | 12/2012 | Pacetti | 623/1.42 |
| 2013/0053947 | A1 * | 2/2013 | Kangas et al. | 623/1.42 |

OTHER PUBLICATIONS

Aytac et al., "Correlation Between the Diameter of the Main Renal Artery and the Presence of an Accessory Renal Artery", J. Ultrasound Med. 22, pp. 433-439 (2003).
Martin et al., "Enhancing the biological activity of immobilized osteopontin using a type-1 collagen affinity coating", J. of Biomed. Mat. Res. vol. 70, issue 1, pp. 10-19 (2004).
Ormiston "A bioabsorbable everolimus-eluting coronary stent system for patients with single de-novo coronary", The Lancent 371, pp. 899-907 (2008).
Ormiston et al.,"Bioabsorbable Coronary Stents", Circ. Cardiovasc. Intervent. 2, pp. 255-260 (2009).
Rini et al., "Renal cell carcinoma", Current Opinion in Oncology 20(3) pp. 300-306 (2008).
Serruys "A bioabsorbable everolimus-eluting coronary stent system (Absorb)", The Lancent 373, pp. 897-910 (2009).
Spagnuolo et al., "Gast is induced by VE-cadherin and vascular endothelial growth factor and inhibits endothelial cell apoptosis", Blood 103, pp. 3005-3012 (2004).
Völkel et al., "Targeting of immunoliposomes to endothelial cells using a single-chain Fv fragment directed against human endoglin (CD105)", Biochimica et Biophysica Acta 1663, pp. 158-166 (2004).

* cited by examiner

*Primary Examiner* — Thomas McEvoy
*Assistant Examiner* — Julie A Szpira
(74) *Attorney, Agent, or Firm* — Squire Sanders (US) LLP (57) ABSTRACT

Methods of treating renal cancers and other kidney-related inflammatory disorders with a bioabsorbable polymer scaffold (such as a stent) are described. The treatments are provided as alternative to complete or partial surgical removal of a diseased kidney.

31 Claims, 4 Drawing Sheets

DRUG-ELUTING BIOABSORBABLE RENAL ARTERY STENT FOR RENAL CANCER AND INFLAMMATORY DISORDERS

FIELD OF THE INVENTION

This invention relates to methods and systems for treating renal cancers and other kidney-related inflammatory disorders using a bioabsorbable polymer scaffold such as implantable polymer stents. In particular, the invention relates methods of delivering therapeutic agents to a diseased kidney via a bioabsorbable polymer scaffold that comprises a polymer matrix and a polymer substrate. The implantable device delivers the therapeutic agents over an extended period of time and is completely absorbed by the body at the end of the duration.

BACKGROUND OF THE INVENTION

Common types of kidney cancer include renal cell carcinoma (RCC) and urothelial cell carcinoma (UCC) of the renal pelvis. Renal cell carcinoma (RCC, also known as hypernephroma) is a kidney cancer that originates in the lining of the proximal convoluted tubule, the very small tubes in the kidney that filter the blood and remove waste products. RCC is the most common type of kidney cancer in adults, responsible for approximately 80% of cases. It is also known to be the most lethal of all the genitourinary tumors.

In addition to renal cell carcinoma and renal pelvis carcinoma, other less common types of kidney cancer include: squamous cell carcinoma, juxtaglomerular cell tumor (reninoma), angiomyolipoma, renal oncocytoma, bellini duct carcinoma, clear-cell sarcoma of the kidney, mesoblastic nephroma, Wilms' tumor (usually reported in children under the age of 5), mixed epithelial stromal tumor. In addition, other types of cancer and potentially cancerous tumors that more usually originate elsewhere can also originate in the kidneys, such as clear cell adenocarcinoma, transitional cell carcinoma, inverted papilloma, renal lymphoma, teratoma, carcinosarcoma, carcinoid tumor of the renal pelvis. Further, cancer in the kidney may also be secondary, the result of metastasis from a primary cancer elsewhere in the body.

Inflammation of the kidney further includes nephritis, lupus nephritis, and pyelonephritis. The two most common causes of nephritis are infection or an auto-immune process. For example, nephritis has the effect of damaging and closing up the microscopic filters in the kidney. This means that in addition to various toxic waste products, the inflamed kidney filters out important proteins (larger molecules) from the blood. Therefore the characteristic symptom of nephritis is proteinuria; the excessive removal of protein from the blood and its excretion in urine.

Initial treatment of kidney cancer (especially RCC) is most commonly a radical or partial nephrectomy (surgical removal of a kidney), which remains the chief method of curative treatment. Where the tumor is confined to the renal parenchyma, the 5-year survival rate is 60-70%. However, this rate is lowered considerably where metastases have occurred. RCC is resistant to radiation therapy and chemotherapy, although some cases respond to immunotherapy. Targeted cancer therapies such as sunitinib, temsirolimus, bevacizumab, interferon-alpha, and possibly sorafenib have improved the outlook for RCC (progression-free survival), although they have not yet demonstrated improved survival. See, for example, Rini et al., 2008, "Renal cell carcinoma," *Curr Opin Oncol* 20 (3): 300-306.

What is needed are methods, systems, and compositions of treating kidney cancers and kidney-related inflammatory disorders in lieu of a complete or partial surgical removal of the vital organ.

INCORPORATION BY REFERENCE

All publications and patent applications mentioned in this specification are hereby incorporated by reference to the same extent as if each individual publication or patent application was specifically and individually indicated to be incorporated by reference, and as if each said individual publication or patent application was fully set forth, including any figures, herein.

SUMMARY OF THE INVENTION

In one aspect, provided herein is a method of treating a kidney-related disease in a human patient. In some embodiments, the method comprises the steps of 1) deploying a bioabsorbable polymer scaffold in the lumen of a blood vessel with direct access to a kidney in a diseased condition in the patient and 2) delivering the therapeutic agent to the diseased kidney over an extended period of time. In some embodiments, the bioabsorbable polymer scaffold eventually completely absorbs away. In some embodiments, the bioabsorbable polymer scaffold comprises a polymer substrate and a polymer matrix coated upon the polymer substrate, both comprising a therapeutic agent.

In some embodiments, the kidney-related disease is a kidney cancer or a kidney-related inflammatory disease.

In some embodiments, the bioabsorbable polymer scaffold is a stent.

In some embodiments, the extended period of time is at least 3 months, 6 months, 9 months, 12 months, 18 months, 24 months, or 36 months.

In some embodiments, the therapeutic agent is everolimus, halofuginone, ruboxistaurin, sirolimus, zotarolimus, temsirolimus, pimecrolimus, biolimus or a combination of these drugs. In some embodiments, the therapeutic agent is everolimus.

In some embodiments, the bioabsorbable polymer scaffold comprises a bioabsorbable polymer that is one or more of poly(DL-lactide), poly(L-lactide), poly(D-lactide), poly(L-lactide-co-D,L-lactide), polymandelide, polyglycolide, poly (lactide-co-glycolide), poly(D,L-lactide-co-glycolide), poly (L-lactide-co-glycolide), poly(ester amide), poly(ortho esters), poly(glycolic acid-co-trimethylene carbonate), poly (D,L-lactide-co-trimethylene carbonate), poly(trimethylene carbonate), poly(lactide-co-caprolactone), poly(glycolide-co-caprolactone), poly(tyrosine ester), polyanhydride, derivatives thereof. In some embodiments, the bioabsorbable polymer scaffold comprises a combination of these polymers.

In some embodiments, the polymer matrix comprises poly (DL-lactide). In some embodiments, the polymer substrate comprises poly(L-lactide). In some embodiments, the therapeutic agent is everolimus. In some embodiments, the ratio of poly(DL-lactide) or poly(L-lactide) to everolimus in the polymer matrix is about 1:1.

In some embodiments, the bioabsorbable polymer scaffold maintains a radial strength of at least 200 mmHg for about 3-6 months.

In some embodiments, prior to deployment, the bioabsorbable polymer scaffolds are constrained at a reduced diameter by a sheath and are deployed by removing the sheath and allowing the scaffolds to self-expand to the increased diameter.

In some embodiments, prior to deployment, the scaffolds are constrained at a reduced diameter around a balloon and are deployed by expanding the balloon which expands the scaffolds to the increased diameter.

In some embodiments, the method provided herein further comprises the step of implanting an additional bioabsorbable scaffold at the site of deployment of at least one of the scaffolds after it has partially or completely absorbed. In these embodiments, the additional scaffold is deployed at a greater diameter than the absorbed scaffold to accommodate for treatment of the diseased kidney.

In another aspect, provided herein is a method of treating a kidney-related disease in a human patient. The method comprises the steps of deploying a bioabsorbable polymer scaffold into the lumen of a blood vessel with direct access to a kidney in a diseased condition in the patient and delivering the first and second therapeutic agent to the diseased kidney over an extended period of time. In some embodiments, the bioabsorbable polymer scaffold comprises a polymer substrate comprising a first therapeutic agent and a polymer matrix coated upon the polymer substrate comprising a second therapeutic agent. In some embodiments, the bioabsorbable polymer scaffold eventually completely absorbs away.

In some embodiments, the first and second therapeutic agents are different. In some embodiments, the extended period of time for the first and second therapeutic agents may be the same or different.

In some embodiments, the extended period of time for the first and the second therapeutic agent is independently at least 3 months, 6 months, 9 months, 12 months, 18 months, 24 months, or 36 months.

In some embodiments, the bioabsorbable polymer scaffold is a stent.

In some embodiments, the bioabsorbable polymer scaffold comprises a bioabsorbable polymer selected from poly(DL-lactide), poly(L-lactide), poly(D-lactide), poly(L-lactide-co-D,L-lactide), polymandelide, polyglycolide, poly(lactide-co-glycolide), poly(D,L-lactide-co-glycolide), poly(L-lactide-co-glycolide), poly(ester amide), poly(ortho esters), poly(glycolic acid-co-trimethylene carbonate), poly(D,L-lactide-co-trimethylene carbonate), poly(trimethylene carbonate), poly(lactide-co-caprolactone), poly(glycolide-co-caprolactone), poly(tyrosine ester), polyanhydride, derivatives thereof, and a combination thereof.

In some embodiments, the polymer matrix comprises poly(DL-lactide) and the second therapeutic agent is everolimus.

In some embodiments, the polymer substrate comprises poly(L-lactide) and the first therapeutic agent is everolimus.

In some embodiments, the first or second therapeutic agent one or more of halofuginone, ruboxistaurin, sirolimus, everolimus, zotarolimus, temsirolimus, pimecrolimus and biolimus.

In some embodiments, the first and second therapeutic agent are everolimus.

In some embodiments, the bioabsorbable polymer scaffold maintains a radial strength of at least 200 mmHg for at least 6 months.

In some embodiments, prior to deployment, the bioabsorbable polymer scaffolds are constrained at a reduced diameter by a sheath and are deployed by removing the sheath and allowing the scaffolds to self-expand to the increased diameter.

In some embodiments, prior to deployment, the scaffolds are constrained at a reduced diameter around a balloon and are deployed by expanding the balloon which expands the scaffolds to the increased diameter.

In some embodiments, the method further comprises implanting an additional bioabsorbable scaffold at the site of deployment of at least one of the scaffolds after it has partially or completely absorbed. In some embodiments, the additional scaffold is deployed at a greater diameter than the absorbed scaffold to accommodate for treatment of the diseased kidney.

DETAILED DESCRIPTION OF THE INVENTION

Provided herein are systems and methods of treating a kidney in a diseased condition, using bioabsorbable implantable device that are adapted to be implanted in a bodily lumen. A system designed for local delivery has the advantage of dose sparing, such that the drug is delivered directly to the kidney lowering the risk of adverse systemic effects. In the present invention, an implantable device such as an implantable stent is used to deliver one or more therapeutic agents to a kidney-related disease. Here, a kidney-related disease includes but are not limited to kidney cancers and other kidney-related inflammatory disorders.

It is understood that use of the singular throughout this application including the claims includes the plural and vice versa unless expressly stated otherwise. That is, "a" and "the" are to be construed as referring to one or more of whatever the word modifies. Non-limiting examples are: "a therapeutic agent" which is understood to include one such agent, two such agents or, under the right circumstances, as determined by those skilled in the treatment of diseased tissues, even more such agents unless it is expressly stated or is unambiguously obvious from the context that such is not intended. Likewise, "a biodegradable polymer" refers to a single polymer or a mixture of two or more polymers unless, again, it is expressly stated or absolutely obvious from the context that such is not intended.

As used herein, "substantial" or "substantially" means that the object of the adjective or adverb is not a perfect example of such object but would be immediately envisaged by the skilled artisan to warrant the general designation. That is, when modified by the word "substantially," it is understood that the object of the modifier would be considered close enough to be recognized by those of ordinary skill in the art as being within the general genus of such objects. As a non-limiting example relating to the current invention, "substantially spherical" refers to an object that, while not a mathematically perfect sphere, would be easily recognized as being within reasonable bounds of that which those skilled in the art would readily consider generally "spherical."

The use of other words or approximation herein, such as "about" or "approximately" when used to describe numerical values or ranges likewise are understood to mean that those skilled in the art would readily consider a value different from the exact number or outside the actual range to be close enough to be within the aegis of that number or range. At the very least, "about" or approximately is understood to mean±15% of a given numerical value or range starting and ending point.

As used herein, "treating" refers to the administration of a therapeutically effective amount of a therapeutic agent to a patient afflicted with a diseased tissue.

A "patient" refers to any species that might benefit from treatment using the method herein but at present is preferably a mammal and most preferably a human being.

As used herein, a "tissue," while generally referring to any group of cells that in the aggregate perform the same function, refers specifically to tissues that receive blood through a dedicated arterial system, such tissues including, without limitation, the lungs (pulmonary artery), liver (hepatic artery), kidneys (renal artery) and heart (coronary artery).

As used herein, a "diseased kidney tissue" refers to a kidney tissue in which there is a disturbance of normal functioning due to a pathological condition characterized by recognizable symptoms and signs.

As used herein, a "therapeutic agent" refers to any substance that, when administered in a therapeutically effective amount to a patient, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease.

A "therapeutically effective amount" refers to that amount of a therapeutic agent that will have a beneficial effect, which may be curative or palliative, on the health and well-being of the patient so afflicted. A therapeutically effective amount may be administered as a single bolus, as intermittent bolus charges, as short, medium or long term sustained release formulations or as any combination of these. As used herein, short-term sustained release refers to the administration of a therapeutically effective amount of a therapeutic agent over a period of about an hour to about 3 days. Medium-term sustained release refers to administration of a therapeutically effective amount of a therapeutic agent over a period of about 3 days to about 4 weeks and long-term refers to the delivery of a therapeutically effective amount over any period in excess of about 4 weeks, but in particular at present about 4 weeks to about a year.

As provided herein, a "bioabsorbable polymer scaffold" refers to a structure made of one or more bioabsorbable polymers. In some embodiments, the bioabsorbable polymer scaffold is an implantable device, such as a stent, a catheter, or a balloon. In some embodiments, the bioabsorbable polymer scaffold comprises a polymer substrate and a polymer matrix. The polymeric matrix is deposited as a coating upon the polymer substrate. In some embodiments, the coating comprises one or more layers in any combination, including but not limited to a primer layer, which may improve adhesion of subsequent layers on the implantable substrate or on a previously formed layer; (b) a reservoir layer, which may comprise a polymer and a therapeutic agent or, alternatively, a polymer free agent; (c) a topcoat layer, which may serve as a way of controlling the rate of release of an agent; and (d) a biocompatible finishing layer, which may improve the biocompatibility of the coating. The polymer matrix and polymer substrate can be completely absorbed by the body, preferably at different rate.

In some embodiments, the bioabsorbable polymer scaffold is radially expandable such as a stent, although one of skill in the art would understand that the scope of this invention is not limited to stents.

As used herein, a "lumen" refers to a cavity of a tubular organ such as a blood vessel. In embodiments of the present invention, a lumen refers to a cavity of a blood vessel such as an artery that is connected to the kidney.

As used herein, a "causal factor" refers to an abnormal biochemical process that at last in part results in the particular tissue disease as manifested by symptoms and signs that characterize the disease.

As used herein, an "artery that directly services the diseased tissue" refers to an artery sufficiently near the diseased tissue that blood entering that artery must proceed by means of the circulatory system into and through the diseased tissue such that the bioabsorbable polymer scaffold of this invention are entrapped entirely or at least predominantly in the target diseased tissue. Such arteries include, without limitation, the coronary artery, the bronchial artery, the hepatic artery and the renal artery.

As used herein, "combining" a therapeutic agent with a biocompatible carrier refers simply to the physical mixing of the agent and the carrier to form a substantially homogeneous mixture.

As used herein a "carrier" refers to the substance that constitutes the continuous phase of a bioabsorbable polymer scaffold, if solid, or the contents of the core if core-shell in structure.

As used herein, "biocompatible" refers to a property of a material characterized by it, or its physiological degradation products, being not, or at least minimally, toxic to living tissue; not, or at least minimally and reparably, otherwise injurious living tissue; and/or not, or at least minimally and controllably, causative of an immunological reaction in living tissue. With regard to salts, both the cation and anion must be biocompatible.

As used herein, a "counterion" refers to an ion of opposite charge to another ion in a salt such that electronic neutrality is maintained. For example, sodium (Na+) is the counterion of chloride (CL−) in common table salt, NaCl, and visa versa.

By "directly services" is meant that blood flowing through the artery proceeds in one direction only through the labyrinthine maze comprising artery→arterioles→metarterioles→capillaries→postcapillary venules→venules→vein. It is noted that the kidneys have a rather unique circulatory system: arteries→afferent arterioles→glomerular capillaries→efferent arterioles, but the methods of this invention are eminently suitable for use with the kidneys as well as other organs.

As used herein, the term "biodegradation" includes all means by which a polymer can be disposed of in a patient's body, which includes bioabsorption, resorption, etc. Degradation occurs through hydrolysis, chemical reactions, or enzymatic reactions. Biodegradation can take place over an extended period of time, for example over 2-3 years. The term "biostable" means that the polymer does not biodegrade or bioabsorb under physiological conditions, or biodegrade or bioabsorb very slowly over a very long period of time, for example, over 5 years or over 10 years.

Physiological conditions merely refers to the physical, chemical and biochemical milieu that constitutes the mammalian body and includes, without limitation, pH, temperature, enzymes and the presence of destructive cells such as phagocytes.

Kidney Structure and Kidney-Related Diseases

In some embodiments, the present systems and methods are used to treat renal cell carcinoma (RCC). In each of the above described conditions, anti-neoplastic therapy delivered directly into the affected kidney is a feasible approach to local treatment of the cancer. Everolimus (Afinitor) is indicated for the treatment of patients with advanced renal cell carcinoma (RCC) after failure of treatment with sunitinib or sorafenib. A range of side effects of such therapy have been described, and reported in the package insert. These include non-infections pneumonitis, infections, oral ulceration etc. In some embodiments, dose-sparing technologies is used to stimulate a strong drug response using less amount of therapeutic agents. These technologies include changing the mode of delivery or adding effect-enhancing adjuvant to the therapeutic compositions. A dose-sparing technology that allows direct delivery of everolimus into the kidney has the advantage of exposing the kidney, and thus the tumor, to high local concentration of drug, minimizing systemic toxicity. For example, delivering the drug via a bioresorbable stent offers the advantage of treating the vasculature with a second stent if necessary, after the first one is resorbed.

In some embodiments, the present systems and methods are used to treat one or more inflammatory disorders of the kidney. The inflammatory disorders include the following: 1) Glomerulonephritis; 2) interstitial nephritis or tubulo-interstitial nephritis; 3) pyelonephritis; 4) lupus nephritis; and 5) chronic allograft rejection. Glomerulonephritis is inflammation of the glomeruli (when the term "nephritis" is used without qualification, this is often the condition meant). Interstitial nephritis or tubulo-interstitial nephritis is inflammation of the spaces between renal tubules. Pyelonephritis is an inflammation that results from a urinary tract infection that reaches the pyelum (pelvis) of the kidney. Lupus nephritis is an inflammation of the kidney caused by systemic lupus erythematosus (SLE), a disease of the immune system. Chronic allograft rejection refers to the long-term loss of function in transplanted organs via fibrosis of the transplanted tissue's blood vessels.

In an aspect of this invention, the kidney disease is selected from the group consisting of chronic kidney disease, diabetic nephropathy, focal segmental glomerulosclerosis, IgA nephritis, lupus nephritis, reflux nephropathy, glomerulonephritis, glumerulonephrosis and polycystic renal disease.

Exemplary Bioabsorbable Polymer Scaffolds

Any bioabsorbable polymer scaffold that can be inserted into a site, such as the lumen of a blood vessel connected to a diseased kidney, can be used to in the present invention. In some embodiments, the bioabsorbable polymer scaffold is an implantable device, such as a stent, a catheter, or a balloon. A stent will be used as an example to illustrate the characteristics of an exemplary bioabsorbable polymer scaffold. However, one of skill in the art would understand that any device made of bioabsorbable polymer that is suitable for delivering one or more therapeutic agents to a diseased kidney can be used in the present invention.

Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Figure 1:
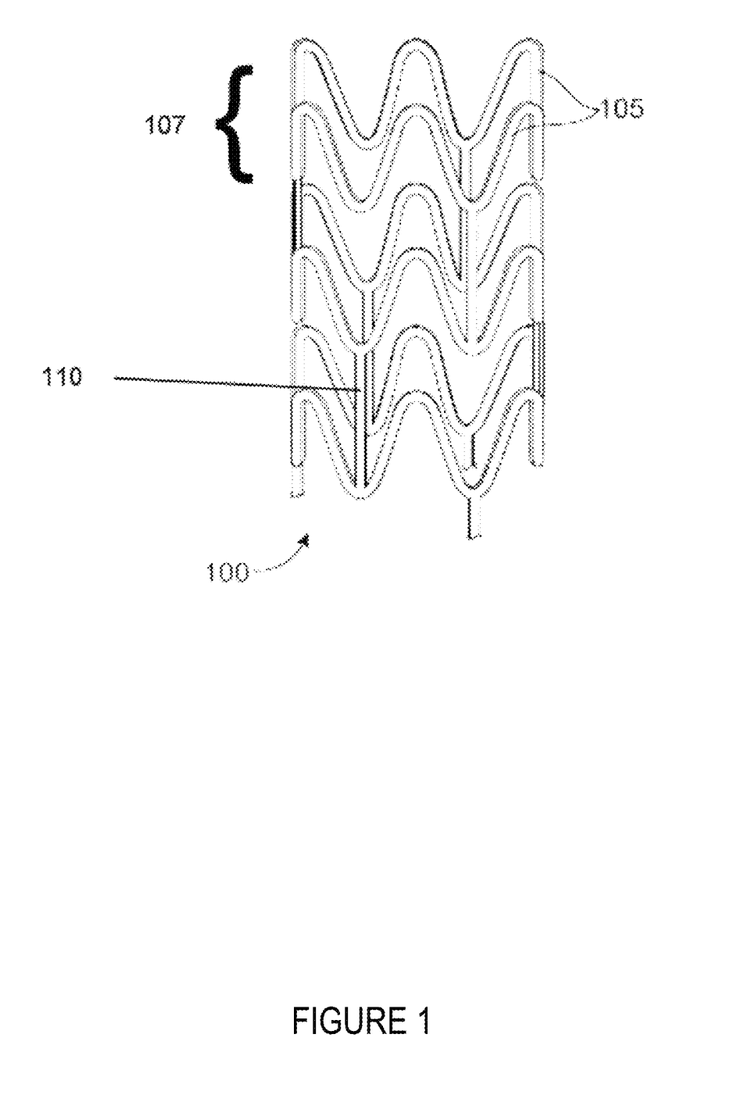
FIG. 1 depicts an exemplary stent scaffolding.
Figure 2:
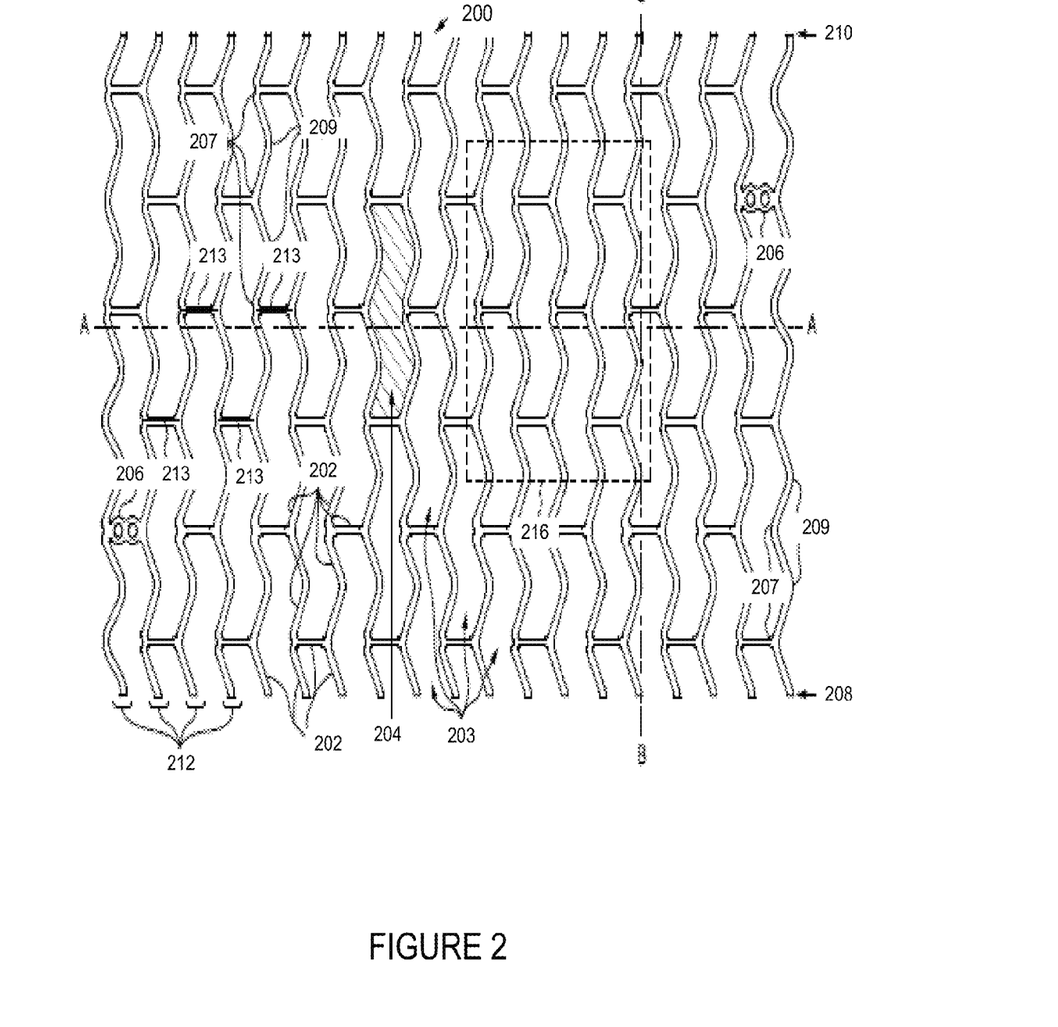
FIG. 2 depicts an exemplary stent pattern shown in a planar or flattened view.

Stents are typically composed of a scaffold or scaffolding that includes a pattern or network of interconnecting structural elements or struts, formed from wires, tubes, or sheets of material rolled into a cylindrical shape (see, for example, FIGS. 1 and 2). This scaffolding gets its name because it physically holds open and, if desired, expands the wall of the passageway. Typically, stents are capable of being compressed or crimped onto a catheter so that they can be delivered to and deployed at a treatment site.

FIG. 1 depicts a view of an exemplary stent 100. In some embodiments, a stent may include a body, substrate, or scaffold having a pattern or network of interconnecting structural elements 105. Stent 100 may be formed from a tube (not shown). FIG. 1 illustrates features that are typical to many stent patterns including undulating sinusoidal cylindrical rings 107 connected by linking elements 110. As mentioned above, the cylindrical rings are load bearing in that they provide radially directed force to support the walls of a vessel. The linking elements generally function to hold the cylindrical rings together. A structure such as stent 100 having a plurality of structural elements may be referred to as a stent scaffold or scaffold. Although the scaffold may further include a coating, it is the scaffolding structure that is the load bearing structure that is responsible for supporting lumen walls once the scaffolding is expanded in a lumen.

The structural pattern in FIG. 1 is merely exemplary and serves to illustrate the basic structure and features of a stent pattern. A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed on a tube or sheet with a technique such as laser cutting or chemical etching. The stent can then be crimped on to a balloon or catheter for delivery into a bodily lumen.

Alternatively, the scaffold design may be composed of radial bands that slide to increase the diameter of the scaffold. Such a design utilizes a locking mechanism to fix the stent at a target diameter and to achieve final radial strength. In other embodiments, the scaffold design could be braided polymer filaments or fibers.

In a preferred embodiment a stent scaffold has the stent pattern described in U.S. Patent Publication No. US 2010/0004735 by Yang & Jow, et al. Other examples of stent patterns suitable for PLLA are found in US Patent Publication No. 2008/0275537. FIG. 2 depicts exemplary stent pattern 200 from US 2008/0275537. The stent pattern 200 is shown in a planar or flattened view for ease of illustration and clarity, although the stent pattern 200 on a stent actually extends around the stent so that line A-A is parallel or substantially parallel to the central axis of the stent. The pattern 200 is illustrated with a bottom edge 208 and a top edge 210. On a stent, the bottom edge 208 meets the top edge 210 so that line B-B forms a circle around the stent. In this way, the stent pattern 200 forms sinusoidal hoops or rings 212 that include a group of struts arranged circumferentially. The rings 212 include a series of crests 207 and troughs 209 that alternate with each other. The sinusoidal variation of the rings 212 occurs primarily in the axial direction, not in the radial direction. That is, all points on the outer surface of each ring 212 are at the same or substantially the same radial distance away from the central axis of the stent.

The stent pattern 200 includes various struts 202 oriented in different directions and gaps 203 between the struts. Each gap 203 and the struts 202 immediately surrounding the gap 203 define a closed cell 204. At the proximal and distal ends of the stent, a strut 206 includes depressions, blind holes, or through holes adapted to hold a radiopaque marker that allows the position of the stent inside of a patient to be determined.

One of the cells 204 is shown with cross-hatch lines to illustrate the shape and size of the cells. In the illustrated embodiment, all the cells 204 have the same size and shape. In other embodiments, the cells 204 may vary in shape and size.

Still referring to FIG. 2, the rings 212 are connected to each other by another group of struts that have individual lengthwise axes 213 parallel or substantially parallel to line A-A. The rings 212 are capable of being collapsed to a smaller diameter during crimping and expanded to their original diameter or to a larger diameter during deployment in a vessel. Specifically, pattern 200 includes a plurality of hinge elements. When the diameter of a stent having stent patter 200 is reduced or crimped, the angles at the hinge elements decrease which allow the diameter to decrease. The decrease in the angles results in a decrease in the surface area of the gaps 203. Dimensions of the stent for renal applications depend upon such factors as the size of the anatomical lumen that is to be treated. In general, for most coronary, renal and pulmonary applications, the diameter of the scaffold is 2 to 8 mm, 4 to 7 mm, 3 to 5 mm, or more narrowly 2.5 to 3.5 mm. In some embodiments, bioabsorbable polymer scaffold of smaller diameters (e.g., less than 2 mm) or larger diameters (e.g., more than 10 mm) may be used. In general the length of the scaffold is 8 to 38 mm, or more narrowly, 8 to 12 mm, 12 to 18 mm, 15 to 18 mm, 18 to 24 mm, 18 to 38 mm. In preferred embodiments, a bioabsorbable polymer scaffold has a diameter of 4-7 mm. In preferred embodiments, a bioabsorbable polymer scaffold has a length at 12 mm, 15 mm or 18 mm. All diameter ranges refer to inner or outer diameter and the as-fabricated or deployed diameter. The scaffolds for renal treatment have sufficient radial strength to support the vessels at a target diameter. The radial strength is a scaffold property and is a complex function of various factors such as scaffold material properties and stent geometry (e.g., strut dimensions, scaffold pattern). In general, scaffolds preferably have a radial strength of 10-900 mmHg, preferably 10-100 mmHg, 20-50 mmHg, 50-100 mmHg, 100-200 mmHg, 200-400 mmHg, 400-600 mmHg, or 600-900 mmHg. Scaffold design, scaffold material, morphology of scaffold material, or any combination thereof can be adjusted to account for different radial strength requirements for different renal cancers and inflammatory disorders.

In some embodiments, the presence of the stent is necessary only for a limited period of time, as the artery undergoes physiological remodeling over time. The development of a bioabsorbable stent or scaffold could obviate the permanent metal implant in vessel, allow late expansive luminal and vessel remodeling, and leave only healed native vessel tissue after the full absorption of the scaffold. Stents fabricated from bioresorbable, biodegradable, bioabsorbable, and/or bioerodable materials such as bioabsorbable polymers can be designed to completely absorb only after or some time after the clinical need for them has ended. Consequently, a fully bioabsorbable stent can reduce or eliminate the risk of potential long-term complications and of late thrombosis, facilitate non-invasive diagnostic MRI/CT imaging, allow restoration of normal vasomotion, provide the potential for plaque regression.

The use of bioabsorbable polymer stents has a number of advantages. (i) The stent disappears from the treated site resulting in reduction or elimination of late stent thrombosis. (ii) Disappearance of the stent facilitates repeat treatments (surgical or percutaneous) to the same site. (iii) Disappearance of the stent allows restoration of vasomotion at the treatment site. The presence of a rigid permanent metal stent restricts vasomotion. (iv) The bioabsorbability results in freedom from side-branch obstruction by struts. (v) The disappearance results in freedom from strut fracture and ensuing restenosis. The progression of stenosis seen within stents 7 to 10 years after stenting has been attributed, at least in part, to inflammation around metallic struts.

With respect to renal application of bioabsorbable stents, since a bioabsorbable stent disappears, normal maintenance of the kidney of the patient is accommodated. The BVS stent bioresorbable polymer stents has been applied to the coronary artery in adults. (Abbott Laboratories, Abbott Park, Ill., USA) made from poly(L-lactide) (PLLA) has undergone two sets of clinical trials. The studies have demonstrated feasibility for treatment of stenosis in coronary arteries; see for example, *Circulation: Cardiovascular Interventions*, 2009, 2: 255-260; *The Lancet*, 2008, 371(9616): 899-907; and *The Lancet* 2009, 373 (9667): 897-910. In the embodiments disclosed herein, bioabsorbable polymer scaffolds (such as stents) can be used to treat adults and children.

Delivering Therapeutic Agents to a Diseased Kidney

The renal arteries normally arise off the side of the abdominal aorta, immediately below the superior mesenteric artery, and supply the kidneys with blood. Each is directed across the crus of the diaphragm, so as to form nearly a right angle with the aorta. The renal arteries carry a large portion of total blood flow to the kidneys. Up to a third of total cardiac output can pass through the renal arteries to be filtered by the kidneys. The arterial supply of the kidneys is variable and there may be one or more renal arteries supplying each kidney. It is located above the renal vein. Supernumerary renal arteries (two or more arteries to a single kidney) are the most common renovascular anomaly, occurrence ranging from 25% to 40% of kidneys. The measured mean diameter can differ depending on the imaging method used. The average diameter has been reported as 5.04±0.74 mm using ultrasound, and 5.68±1.19 mm using angiography. See, for example, Aytac et al. 2003, "Correlation between the diameter of the main renal artery and the presence of an accessory renal artery: sonographic and angiographic evaluation." *J Ultrasound Med.* 22(5):433-9. Exemplary illustrations of the kidney can be found in FIGS. 4A and 4B.

In some embodiments, a bioabsorbable polymer scaffold is placed in a lumen of a tubular structure or cavity (such as a blood vessel) that is connected to a diseased kidney. In some embodiments, the tubular structure is a renal artery, an internal iliac artery, a renal vein, or the ureter. In preferred embodiments, the tubular structure is a renal artery, such as one or more supernumerary renal arteries. In some embodiments, the tubular structure is a branched artery of the renal artery that is connected with the diseased kidney.

Figure 4A:
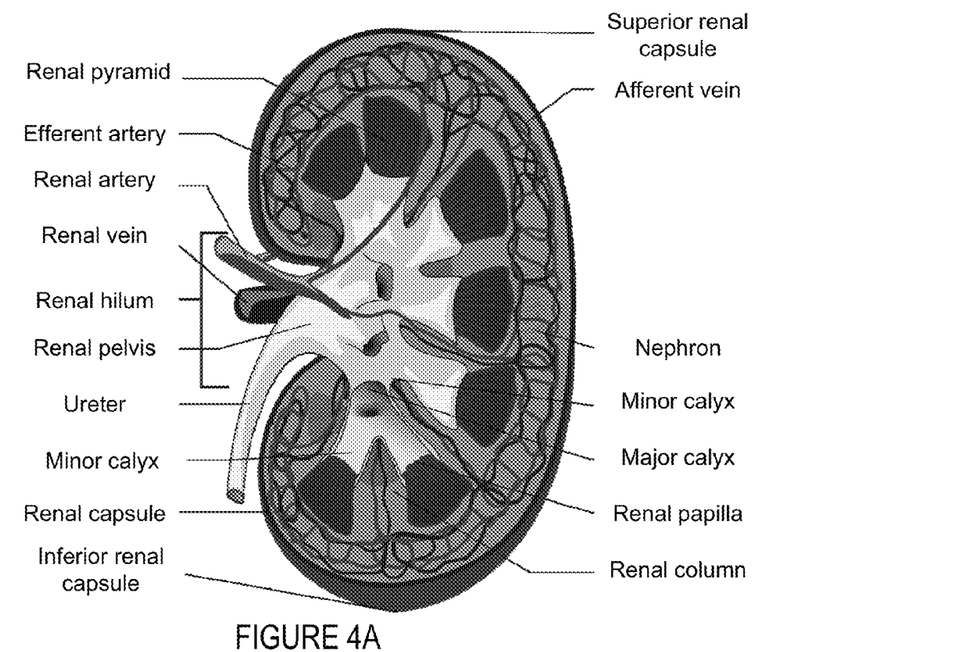
FIGS. 4A and 4B depict structures of kidney.
Figure 4B:
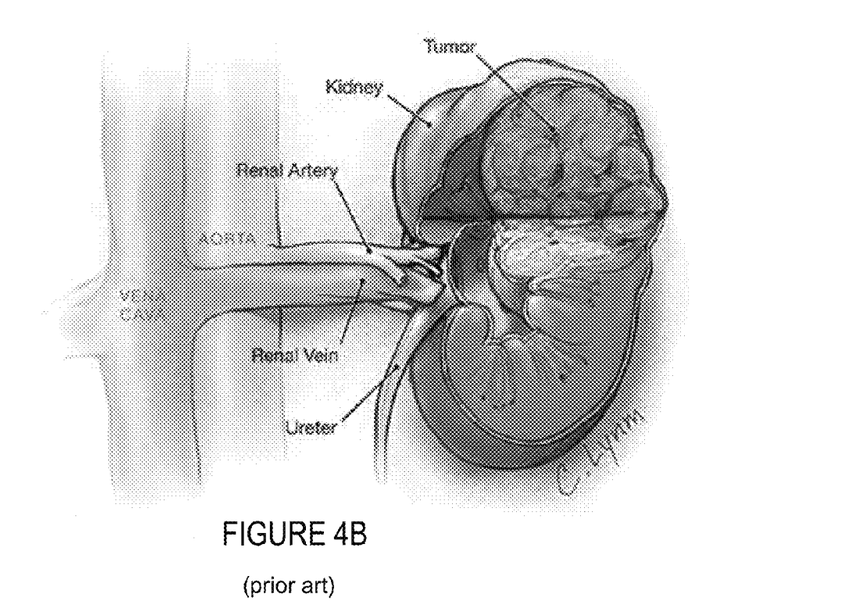

In some embodiments, a bioabsorbable polymer scaffold is placed in a cavity within, for example, renal papilla, renal pelvis, renal cortex, renal medulla, renal capsule, minor calyx, major calyx, renal column, and renal pyramid (FIGS. 4A and 4B). In some embodiments, the cavity is formed naturally or artificially. For example, in some embodiments, a cavity can be created surgically within a diseased area in a kidney (for example, where a tumor or inflammation is located).

In some embodiments, a bioabsorbable polymer scaffold is inserted directly into a renal artery. In some embodiments, a bioabsorbable polymer scaffold is inserted into an peripheral artery and threaded through until it is intersects the renal artery. In some embodiments, a bioabsorbable polymer scaffold is inserted in a surgically-created cavity in the kidney.

In some embodiments, delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty.

Stents are used not only for mechanical intervention but also as vehicles for providing biological therapy. Biological therapy uses medicated stents to locally administer a therapeutic substance. The therapeutic substance can also mitigate an adverse biological response to the presence of the stent. A medicated stent may be fabricated by coating the surface of either a metallic or polymeric scaffolding with a polymeric carrier that includes an active or bioactive agent or drug. Polymeric scaffolding may also serve as a carrier of an active agent or drug. In some embodiments, the therapeutic agent may be mixed or dispersed in part of or throughout the bioabsorbable polymer scaffold, including both the polymer matrix and the polymer substrate.

In embodiments of the present invention, the stent must be able to satisfy a number of mechanical requirements. The stent must be have sufficient radial strength so that it is capable of withstanding the structural loads, namely radial compressive forces imposed on the stent as it supports the walls of a vessel. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation.

Once expanded, the stent must adequately provide lumen support or maintain its expanded diameter during a time required for treatment in spite of the various forces that may come to bear on it, including the cyclic loading induced by the beating heart. In addition, the stent must possess sufficient flexibility with a certain resistance to fracture.

In some instances, a stent may be used primarily for drug delivery. In certain embodiments, the radial strength required for the present invention may be enough to secure the stent (or a similar device) at the desired locale for drug delivery purposes without expanding or significantly expanding the size of the locale or site where the stent is placed (e.g., a renal artery). In some embodiments, the locale or site remains its original size. In some embodiments, the diameter of the locale or site is only slightly greater than its original size in order to secure the stent; for example, by about 15% or less, 12% or less, 10% or less, 8% or less, 5% or less, 3% or less, 2% or less, 1% or less, between 1 and 15%, between 2 and 12%, between 5 and 10%.

The bioabsorbable polymer scaffold is made of one or more bioabsorbable polymers as disclosed herein. In some embodiments, the scaffold is an implantable device, such as a stent, a balloon or a catheter. In some embodiments, the bioabsorbable polymer scaffold comprises a polymer substrate and a polymer matrix; see, for example, FIG. 3 where 310 depicts a sectional view of a part of the bioabsorbable polymer scaffold. The polymeric matrix (e.g., 320) is deposited as a coating upon the polymer substrate (e.g., 330). In some embodiments, the coating comprises one or more layers in any combination, including but not limited to a primer layer, a reservoir layer, a topcoat layer, or a biocompatible finishing layer, which may improve the biocompatibility of the coating. In some embodiments, the polymer matrix is made of an amorphous polymer or an amorphous mixed of polymers. In some embodiments, the polymer substrate is made of a crystalline form of polymer or crystalline form of mixed of polymers. In some embodiments, the bioabsorbable polymer scaffold comprises only a polymer substrate without a polymer matrix coating.

In some embodiments, one or more therapeutic agents are embedded or impregnated in the polymer substrate and polymer matrix. In some embodiments, one or more therapeutic agents are embedded or impregnated only in the polymer matrix. The scaffold may be free of therapeutic agent or a particular type of therapeutic agent other than incidental diffusion of agent into the scaffold from the polymer matrix. In some embodiments, one or more therapeutic agents are embedded or impregnated only in the polymer substrate. The polymer matrix may be free of therapeutic agent or a particular type of therapeutic agent other than incidental diffusion of agent into the scaffold from the scaffold. In some embodiments, the polymer matrix is absent from the bioabsorbable polymer scaffold, and one or more therapeutic agents are embedded or impregnated in the polymer substrate alone.

Everolimus is used here for purposes of illustration; however, one of skill in the art would understand that the principle and mechanism described herein are applicable to all therapeutic agents suitable for treating kidney cancers and inflammatory disorders.

In some embodiments, everolimus is used as the therapeutic agent, for treatment of renal cancer. Advantageously, a bioabsorbable polymer scaffold comprising a therapeutic agent such as everolimus is used in lieu of a total or partial nephrectomy. In some embodiments, the bioabsorbable polymer scaffold is used under the following conditions: 1) early stage renal cancer where a partial nephrectomy results in complete excision of the tumor; 2) malignancy occurring in a patient with poor renal function where removal of a kidney might result in the patient requiring dialysis; 3) malignancy in a solitary kidney; and 4) advanced renal cancer where treatment is palliative and therefore the kidney is not removed.

In some embodiments, everolimus is used as the therapeutic agent, for treating an inflammatory disorder. Everolimus has been shown to have anti-inflammatory properties in tissues such as vascular plaque. A local anti-inflammatory effect in the kidney is likely to have beneficial effects in chronic renal inflammatory states.

One of skill in the art would understand that any therapeutic agents disclosed herein can be used in treating kidney cancers and inflammatory disorders.

In some embodiments, a therapeutic agent is delivered to the site of action (e.g., a lumen of a tubular structure such as a blood vessel that is connected to a diseased kidney) from both the polymer matrix and polymer substrate of the bioabsorbable polymer scaffold. In some embodiments, the therapeutic agent is delivered to the site of action in a two-stage process in which the therapeutic agent is released from the polymer matrix and polymer substrate at different rates.

Figure 3:
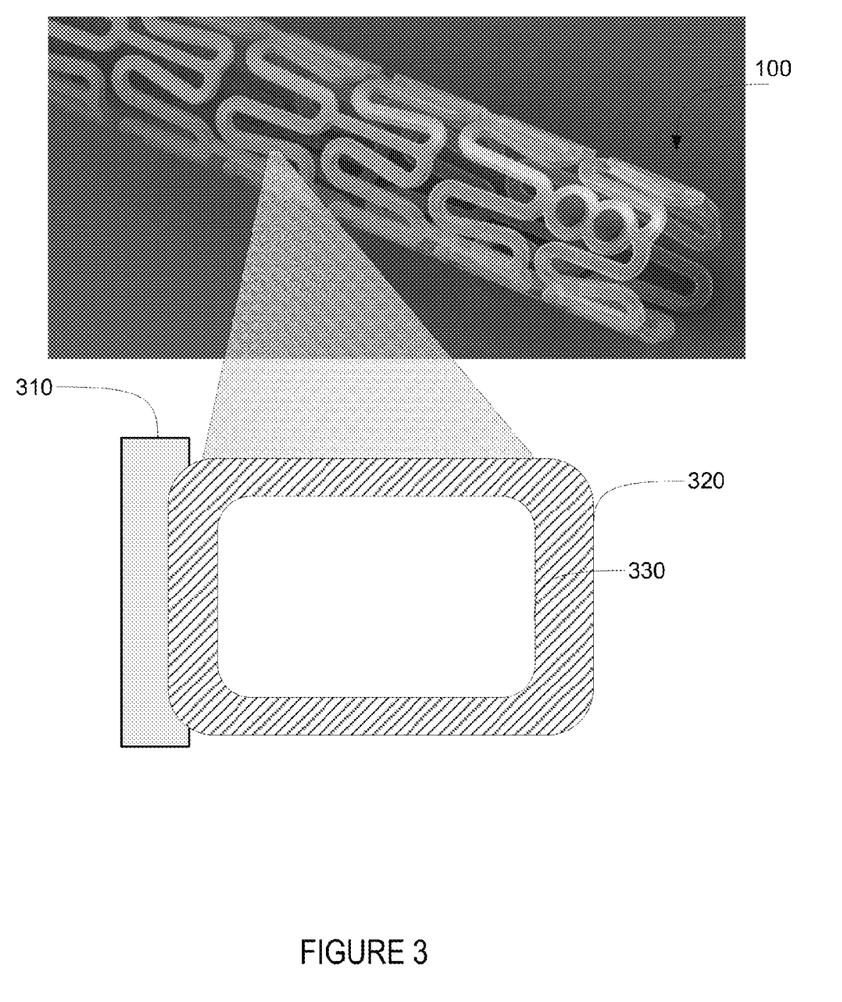
FIG. 3 depicts an exemplary stent scaffolding.

In some embodiments, the polymer matrix (such as a coating) is a thin coating layer that comprises an amorphous (non-crystalline) polymer such as poly(DL-lactide), PDLLA. In some embodiments, the polymer matrix comprises a therapeutic agent. The ratio of the therapeutic agent (e.g., everolimus):polymer matrix (e.g., PDLLA) is about 1:1. In some embodiments, the conformal coating has a thickness (e.g., as illustrated by 320) of less than about 1 µm, between about 1-2 µm, between about 2-3 µm, between about 2-4 µm, between about 1-4 µm, between about 1-5 µm, between about 4-5 µm, or over about 5 µm. In an exemplary embodiment, amorphous PDLLA and everolimus (at a ratio of about 1:1) are combined to form a thin matrix coating layer that is between 2-4 µm. The coating releases the everolimus in a time-controlled manner over an extended period of time (as disclosed herein).

In some embodiments, polymers forming the substrate of the bioabsorbable polymer scaffold are highly crystalline such that it provides structure integrity to the bioabsorbable polymer scaffold. In some embodiments, the polymers used to form the substrate comprise poly(L-lactide), PLA. In some embodiments, the polymer substrate is processed for increased radial strength. In some embodiments, the polymer substrate also comprises a therapeutic agent. In some embodiments, the crystallinity of the polymer forming the polymer substrate is between about 20% and 60%. In some embodiments, the crystallinity of the polymer forming the polymer substrate is between about 30% and 60%. In some embodiments, the crystallinity of the polymer forming the polymer substrate is between about 40% and 60%. In some embodiments, the crystallinity of the polymer forming the polymer substrate is between about 40% and 50%. In some embodiments, the crystallinity of the polymer forming the polymer substrate is between about 35% and 45%. In an exemplary embodiment, crystalline PLLA and everolimus are combined to form the polymer substrate. The substrate is highly crystalline and provides structure integrity to the bioabsorbable polymer scaffold. The bioabsorbable polymer scaffold is processed for increased radial strength.

In some embodiments, the therapeutic agent in the polymer substrate is the same as the one in the polymer matrix coating. In some embodiments, the therapeutic agent in the polymer substrate is different from the one in the polymer matrix coating. In some embodiments, the polymer substrate comprises more than one therapeutic agents. In some embodiments, the polymer matrix coating also comprises more than one therapeutic agents. In some embodiments, the polymer matrix coating and polymer substrate share at least one common therapeutic agent. In some embodiments, the polymer matrix coating and polymer substrate do not share at least one common therapeutic agent.

In some embodiments, a therapeutic agent is released from the polymer matrix and/or polymer substrate of the bioabsorbable polymer scaffold in a controlled fashion over an extended period of time.

In some embodiments, delivery of the therapeutic agent correlates with the absorption or degradation of the polymer matrix and polymer substrate.

In some embodiments, a therapeutic agent is released from the polymer matrix and polymer substrate at the same time with the substrate having a longer lasting release profile, but at different rates. In some embodiments, a therapeutic agent is released from the polymer matrix and polymer substrate at the same time at similar rates: release from the polymer matrix has a shorter-release profile due to, for example, the smaller dimension of the polymer matrix (e.g., a thin coating) and the substrate has a longer lasting release profile due to, for example, the larger dimension of the polymer substrate.

In some embodiments, the therapeutic agent is delivered to the site of action in a two-stage process in which the therapeutic agent is released from the polymer matrix and polymer substrate in an overlapping manner or nearly sequential manner. In some embodiments, the polymer matrix is partially or completely absorbed before the polymer substrate started to be absorbed.

In some embodiments, a therapeutic agent (e.g., everolimus) is initially eluted from the polymer matrix, such as a poly(DL-lactide) coating, over a period of 1-2 months, 2-3 months, 3-4 months, 4-5 months, 5-6 months, or over 6 months. Everolimus is eluted from the polymeric substrate over a longer period of time, for example, over a period of 2 months or longer, 3 months or longer, 4 months or longer, 5 months or longer, 6 months or longer, 8 months or longer, 10 months or longer, 12 months or longer, 15 months or longer, 18 months or longer, 21 months or longer, 24 months or longer, 27 months or longer, 30 months or longer, 36 months or longer, 48 months or longer, or 60 months or longer.

Additional Characteristics of Bioabsorbable Polymer Scaffolds

Bioabsorbable polymer scaffolds include, but are not limited to, self-expandable stents, balloon-expandable stents, stent-grafts, and generally tubular medical devices in the treatment of kidney cancers and/or kidney-related inflammatory disorders. The present invention is further applicable to various stent designs including wire structures, and woven mesh structures.

Self expandable or self expanding stents include a bioabsorbable polymer scaffold that expands to the target diameter upon removal of an external constraint without assistance of a radial outward force. However, self-expandable stents can be assisted by such a radial outward force. The self expanding scaffold returns to a baseline configuration (diameter) when an external constraint is removed. This external constraint could be applied with a sheath that is oriented over a compressed scaffold. The sheath is applied to the scaffold after the scaffold has been compressed by a crimping process. After the stent is positioned at the implant site, the sheath may be refracted by a mechanism that is available at the end of the catheter system and is operable by the physician. The self expanding bioabsorbable scaffold property is achieved by imposing only elastic deformation to the scaffold during the manufacturing step that compresses the scaffold into the sheath.

The bioabsorbable scaffold may also be expanded by a balloon. In this embodiment the scaffold is plastically deformed during the manufacturing process to tightly compress the scaffold onto a balloon counted on a catheter system. The scaffold is deployed at the treatment site by inflation of the balloon. The balloon will induce areas of plastic stress in the bioabsorbable material to cause the scaffold to achieve and maintain the appropriate diameter on deployment.

A stent scaffold can include a plurality of cylindrical rings connected or coupled with linking elements. For example, the rings may have an undulating sinusoidal structure. When deployed in a section of a vessel, the cylindrical rings are load bearing and support the vessel wall at an expanded diameter or a diameter range due to cyclical forces in the vessel. Load bearing refers to the supporting of the load imposed by radial inwardly directed forces. Structural elements, such as the linking elements or struts, are generally non-load bearing, serving to maintain connectivity between the rings. For example, a stent may include a scaffold composed of a pattern or network of interconnecting structural elements or struts.

The prevailing mechanism of degradation of many bioabsorbable polymers is chemical hydrolysis of the hydrolytically unstable substrate. In a bulk degrading polymer, the polymer is chemically degraded throughout the entire polymer volume. As the polymer degrades, the molecular weight decreases. The reduction in molecular weight results in changes in mechanical properties (e.g., strength) and stent properties. For example, the strength of the scaffold material and the radial strength of the scaffold is maintained for a period of time followed by an gradual or abrupt decrease. The decrease in radial strength is followed by a loss of mechanical integrity and then erosion or mass loss. Mechanical integrity loss is demonstrated by cracking and by fragmentation. Enzymatic attack and metabolization of the fragments occurs, resulting in a rapid loss of polymer mass.

The bioresorption properties include not only to the rate of chemical degradation of the scaffold material, but also the rate of loss of mechanical properties, in particular, the radial strength. Bioresorption properties include the total resorption time, the time for the scaffold to absorb away completely from the implant site. Bioresorption properties also include the time that radial strength is maintained. During this period the scaffold can support a lumen at an increased diameter.

Therefore, the behavior of a bioabsorbable stent upon implantation can divided into three stages of behavior. In stage I, the stent provides mechanical support. The radial strength is maintained during this phase. Also during this time, chemical degradation occurs which decreases the molecular weight. In stage II, the scaffold experiences a loss in strength and mechanical integrity. In stage III, significant mass loss occurs after hydrolytic chain scission yields water-soluble low molecular weight species.

The scaffold in the first stage provides the clinical need of providing mechanical support to maintain patency or keep a vessel open at or near the deployment diameter. In some treatments, the patency provided by the scaffold allows the stented segment of the vessel to undergo positive remodeling at the increased deployed diameter. Remodeling refers generally to structural changes in the vessel wall that enhances its load-bearing ability so that the vessel wall in the stented section can maintain an increased diameter in the absence of the stent support. A period of patency is required in order to obtain permanent positive remodeling.

In embodiments of the present invention, the bioresorption properties of scaffolds are adjusted for treatment of kidney cancers or kidney-related inflammatory disorders. The scaffold biodegradation properties such as the resorption time and the support time support are adjusted depending on the clinical need for various conditions. The support time may be dictated by one or more considerations, depending on the treatment, such as remodeling of the vessel, time needed for therapeutic agent to be released into the diseased kidney, for example, into the region of where the kidney tumor is located. A bioabsorbable polymer stent may be used to keep blood vessels open for a period of time, followed which resorption which allows the diseased kidney to recover from the inflammatory disorder, or to inhibit the growth of the tumor.

The manufacturing process of a bioabsorbable scaffold includes selection of a bioabsorbable polymer raw material or resin. Detailed discussion of the manufacturing process of a bioabsorbable stent can be found elsewhere, e.g., U.S. Patent Publication No. 20070283552. The fabrication methods of a bioabsorbable stent can include the following steps:

(1) forming a polymeric tube from a biodegradable polymer resin using extrusion,
(2) radially deforming the formed tube to increase radial strength,
(3) forming a stent scaffolding from the deformed tube by laser machining a stent pattern in the deformed tube with laser cutting, in exemplary embodiments, the strut thickness can be 100-200 microns, or more narrowly, 120-180, 130-170, or 140-160 microns,
(4) optionally forming a therapeutic coating over the scaffolding,
(5) crimping the stent over a delivery balloon, and
(6) sterilization with election-beam (E-beam) radiation.

Poly(L-lactide) (PLLA) is attractive as a stent (e.g., as the substrate or scaffold material) due to its relatively high strength and a rigidity at human body temperature, about 37° C. Since it has a glass transition temperature between about 60 and 65° C. (Medical Plastics and Biomaterials Magazine, March 1998), it remains stiff and rigid at human body temperature. This property facilitates the ability of a PLLA stent scaffold to maintain a lumen at or near a deployed diameter without significant recoil (e.g., less than 10%). In general, the Tg of a semi-crystalline polymer can depend on its morphology, and thus how it has been processed. Therefore, Tg refers to the Tg at it relevant state, e.g., Tg of a PLLA resin, extruded tube, expanded tube, and scaffold.

Additional exemplary biodegradable polymers for use with a bioabsorbable polymer scaffolding include poly(D-lactide) (PDLA), polymandelide (PM), polyglycolide (PGA), poly(L-lactide-co-D,L-lactide) (PLDLA), poly(D,L-lactide) (PDLLA), poly(D,L-lactide-co-glycolide) (PLGA) and poly (L-lactide-co-glycolide) (PLLGA). With respect to PLLGA, the stent scaffolding can be made from PLLGA with a mole % of GA between 5-15 mol %. The PLLGA can have a mole % of (LA:GA) of 85:15 (or a range of 82:18 to 88:12), 95:5 (or a range of 93:7 to 97:3), or commercially available PLLGA products identified as being 85:15 or 95:5 PLLGA. The examples provided above are not the only polymers that may be used. Many other examples can be provided, such as those found in Polymeric Biomaterials, second edition, edited by Severian Dumitriu; chapter 4.

Polymers that are more flexible or that have a lower modulus that those mentioned above may also be used. Exemplary lower modulus bioabsorbable polymers include, polycaprolactone (PCL), poly(trimethylene carbonate) (PTMC), polydioxanone (PDO), poly(4-hydroxy butyrate) (PHB), and poly (butylene succinate) (PBS), and blends and copolymers thereof.

In exemplary embodiments, higher modulus polymers such as PLLA or PLLGA may be blended with lower modulus polymers or copolymers with PLLA or PLGA. The blended lower modulus polymers result in a blend that has a higher fracture toughness than the high modulus polymer. Exemplary low modulus copolymers include poly(L-lactide)-b-polycaprolactone (PLLA-b-PCL) or poly(L-lactide)-co-polycaprolactone (PLLA-co-PCL). The composition of a blend can include 1-5 wt % of low modulus polymer.

As indicated above, the radial strength of the finished stent product (at time of implantation before bioresorption begins) depends on factors such as scaffold material properties and stent geometry. It has been found that radial strength depends on the initial molecular weight or molecular weight at the time of implantation (e.g., Mn(time=0) or Mn(0)). For a given set of factors other than Mn(0), Mn(0) may be adjusted to provide a radial strength that will support a lumen at a target diameter, for example, a radial strength of at least 200 mmHg.

It has been found that the scaffold biodegradation properties, the resorption time and the support time, also depend on the Mn(0) of the scaffold. Mn(0) can be adjusted to provide desired resorption time and support time. It has also been found that the monomer content of the bioabsorbable scaffold material can be adjusted to provide desired resorption time and support time. Specifically, it has been shown that the degradation profile of poly(L-lactide) is strongly dependent on Mn(0) and the degradation rate constant of PLLA, U.S. patent application Ser. No. 13/104,732.

Studies showed that the degradation rate constant of PLLA is strongly dependent on the L-lactide (LLA) monomer content. The hydrolytic degradation of a PLLA scaffold increases with an increase in LLA monomer content. As a result, the Mn and radial strength as a function of time also depend on LLA monomer content. Increasing Mn(0) at implantation increases the support time and the resorption time, while decreasing the Mn(0) has the opposite effect. Increasing the monomer content accelerates the decrease in Mn, thus decreasing support time and resorption time. Increasing the monomer content slows down the decrease in Mn, thus increasing support time and resorption time.

Therefore, the Mn(0), monomer content, or both of the bioabsorbable polymer scaffold can be adjusted to obtain a support time of at least 3, at least 6 months, 1-3 months, 2-3 months, 3 to 6 months. The Mn(0), monomer content, or both of the bioabsorbable scaffold can be adjusted to maintain a radial strength of at least 200 mmHg, at least 400 mmHg, at least 600 mmHg, 200 to 400 mmHg, or 200 to 600 mmHg.

An exemplary PLLA scaffold may have an initial L-lactide monomer content within the range of less than 0.02 wt %, 0.02 to 0.2 wt %, and 0.02 wt % to 1 wt %, or any sub-range or value in these ranges. The Mn(0) can be at least 60 kDa, 60 to 66 kDa, 66 to 80 kDa, 80 to 120 kDa, greater than 120 kDa or any sub-range or value in these ranges. An exemplary PLLA scaffold can have any combination of these Mn(0) and L-lactide monomer content.

The term "molecular weight" can refer to one or more definitions of molecular weight. "Molecular weight" can refer to the molecular weight of individual segments, blocks, or polymer chains. "Molecular weight" can also refer to weight average molecular weight or number average molecular weight of types of segments, blocks, or polymer chains.

The number average molecular weight (Mn) is the common, mean, average of the molecular weights of the individual segments, blocks, or polymer chains. Molecular weight is typically expressed in grams/mole which is referred to as "Daltons." It is determined by measuring the molecular weight of N polymer molecules, summing the weights, and dividing by N:

$$\overline{M}_n = \frac{\sum_i N_i M_i}{\sum_i N_i}$$

where Ni is the number of polymer molecules with molecular weight Mi. The weight average molecular weight is given by $$\overline{M}_w = \frac{\sum_i N_i M_i^2}{\sum_i N_i M_i}$$

where Ni is the number of molecules of molecular weight Mi Unless otherwise specified, "molecular weight" will refer to number average molecular weight (Mn).

Embodiments of the present invention include methods of treating peripheral inflammation in a kidney of a human patient with a bioabsorbable polymer scaffold. In some embodiments, peripheral inflammation is a diseased condition found in the artery branches connected or adjacent to the kidney. Such branches exhibit narrowed segments of one or more of the main or peripheral branches of the renal artery. The branches include those of the main renal artery, and then second and third order branches that feed the more peripheral areas of the kidney.

The method includes identifying segments in one or more peripheral branches of the renal artery of the patient that are narrowed. Narrowed segments are identified by renal angiography. Segments are characterized as narrowed on the basis of clinical examination and angiographic findings of narrowed vessels in the peripheral areas of the kidney. A peripheral branch can have one or more narrowed segments. As a result, the diameter of a bioabsorbable polymer scaffold should be adjusted based on the location where it is introduced.

The method further includes deploying bioabsorbable polymer scaffolds in one or more of the narrowed segments in the one or more peripheral branches near a diseased kidney. In some embodiments, more than one bioabsorbable polymer scaffolds are introduced in a branch. The bioabsorbable polymer scaffolds can be used to introduce the same therapeutic agent over a longer period of time (e.g., longer than the life time of a particular bioabsorbable polymer scaffold)

In some embodiments, the scaffolds deployed in the one or more peripheral renal branches completely absorb away in less than 1 year, less than 2 years, between 1 to 2 years, between 1.5 to 2 years, between 2 to 2.5 years, or greater than 2.5 years. The support time and the resorption time of a scaffold can be adjusted through initial molecular weight of the scaffold material, monomer content of the scaffold material, or both. For example, the scaffold material is PLLA and the LLA monomer content is adjusted.

The target diameter range of the deployed scaffolds, which can correspond, but not necessarily, to the diameter of the scaffolds as fabricated before crimping, can be between 2 and 8 mm, or more narrowly 2 to 5 mm. The target diameter can be based on a diameter that can be determined or is known to provide therapeutic agents to a diseased kidney in a patient. In some embodiments, the target diameter can be the same for all deployed scaffolds. In other embodiments, the target diameters can be different for different scaffolds. In such embodiments, the target diameters of the scaffolds are tailored to a desired size that facilitates the treatment. For example, the scaffolds have sizes that are based on what is known to provide therapeutic agents to a diseased kidney in a patient.

The length of the scaffolds can be between 4 and 40. In some embodiments, when multiple scaffolds are used, the lengths of the scaffolds are the same. In other embodiments, the length of the scaffolds can be different. In such embodiments, the length of the scaffold can be tailored to the length of the narrowed segment.

In some embodiments, bioabsorbable polymer scaffolds can be introduced into surgically created cavity with any area of the kidney where a tumor is located (e.g., FIGS. 4A and 4B). In these embodiments, bioabsorbable polymer scaffolds deliver therapeutic agents directly to the diseased area within the diseased kidney in order to achieve high efficiency.

In further embodiments, the support time for each scaffold is the same. In other embodiments, the support time for the scaffolds can be different in different segments.

The method of treatment may further include implanting at least one additional bioabsorbable scaffold at the site of deployment of at least one of the scaffolds after it has partially or completely absorbed. The additional scaffold may be deployed at a greater diameter than the initial scaffold to accommodate for drug delivery to a diseased kidney.

In further embodiments, the method can include performing surgical repair in the heart 1 to 2 years after implantation. In such embodiments, the surgical repair may be performed after all of the scaffolds have completely absorbed. In other embodiments, the surgical report is performed prior to resorption of at least some of the scaffolds.

The scaffold maintains support of the segment for a period of at least 3, 5, 6, 8, 12, or greater than 12 months. The support time can correspond to a time determined to be necessary for delivering therapeutic agents to a diseased kidney.

In some embodiments, the scaffold completely absorbs away in less than 1 year, less than 2 years, between 1 to 2 years, between 1.5 to 2 years, between 2 to 2.5 years, or greater than 2.5 years. The support time and the resorption time of the scaffold can be adjusted through initial molecular weight, monomer content, or both.

In some embodiments, the scaffold completely absorbs away in less than 1 year, less than 2 years, between 1 to 2 years, between 1.5 to 2 years, between 2 to 2.5 years, or greater than 2.5 years. The support time and the resorption time of the scaffold can be adjusted through initial molecular weight, monomer content, or both.

The method includes deploying a bioabsorbable polymer scaffold at the narrowed segment. The bioabsorbable scaffold provides support at the segment at an increased diameter. The scaffold can maintain a radial strength of at least 200 mmHg for at least 6 months and maintain the support of the segment.

The scaffolds used in the treatments discussed herein are coated with one or more therapeutic agents, including an antiproliferative, anti-inflammatory or immune modulating, anti-migratory, anti-thrombotic or other pro-healing agent or a combination thereof. The anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin I1, actinomycin X1, and actinomycin C1), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof.

In some embodiments, the scaffolds can include a prohealing material. The prohealing material can be dispersed within a bioabsorbable polymer. A prohealing material refers to a material that has the property that it promotes or enhances re-endothelialization of arterial lumen to promote healing of the vascular tissue. The prohealing-containing portions of the scaffold can attract, bind and eventually become encapsulated by endothelial cells. In certain embodiments, the prohealing-containing portions of the stent attract, bind, and become encapsulated by endothelial progenitor cells. The attraction, binding, and encapsulation of the cells will reduce or prevent the formation of emboli or thrombi due to the loss of the mechanical properties that could occur if the scaffold was insufficiently encapsulated. In some embodiments, the enhanced re-endothelialization promotes the endothelialization at a rate faster than the loss of mechanical properties of the scaffold.

In some embodiments, the prohealing material can be dispersed in the body of the bioabsorbable polymer substrate or scaffold. The prohealing material can also be dispersed within a bioabsorbable polymer coating over a surface of a scaffold.

In some embodiments, the prohealing material can be an endothelial cell (EDC) binding agent. In some embodiments, the EDC binding agent can be protein, peptide and antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways (see, e.g., Martin, S. M., et al., *J. Biomed. Mater. Res.* 70A:10-19 (2004)). Endothelial cells can be selectively targeted (for the targeted delivery of immunoliposomes) using scFv A5 (Volkel, T., et al., *Biochimica et Biophysica Acta* 1663:158-166 (2004)). Junction membrane protein vascular endothelial (VE)-cadherin has been shown to bind to endothelial cells and down regulate apoptosis of the endothelial cells (Spagnuolo, R., et al., *Blood* 103:3005-3012 (2004)).

In some embodiments, the EDC binding agent can be the active fragment of osteopontin, (Asp-Val-Asp-Val-Pro-Asp-Gly-Asp-Ser-Leu-Ala-Trp-Gly) (SEQ ID NO:1). Other useful EDC binding agents include EPC (epithelial cell) antibodies, RGD peptide sequences, RGD mimetics, and combinations thereof.

The EDC binding protein and peptide can be prepared according to the established methods, e.g., isolation and purification from natural sources, recombinant techniques, or combinatorial chemistry for the synthesis of peptides. For example, the active fragment of osteopontin can be readily prepared by combinatorial synthesis using, e.g., solid-phase peptide sequencing (e.g., a Merrifield synthesis). The scFv A5 protein can be synthesized by gene expression as described in the literature from the HisCysForNot (5'-TAG TGC GGC CGC TTA GCA TGC TCC GCC ATG GTG ATG GTG ATG ATG CGC ACG TTT GAT TTC CAG TTT GGT-3') (SEQ ID NO:2) (Volkel, T., et al. 2004, *Biochimica et Biophysica Acta* 1663:158-166).

In further embodiments, the prohealing material may a substance or agent that attracts and binds endothelial progenitor cells. Representative substances or agents that attract and bind endothelial progenitor cells include antibodies such as CD-34, CD-133, and vegf type 2 receptor. An agent that attracts and binds endothelial progenitor cells can include a polymer having nitric oxide donor groups.

In other embodiments, the EDC binding agent can be chemically linked to a polymer (e.g., via a linkage). The polymer can be the polymer of the coating or a polymer from which the device is made. For example, the active fragment of osteopontin can be attached to the acid terminal poly(lactic acid) via a PEG linkage.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

Polymeric Material

Among biocompatible, relatively biostable polymers useful as carriers for the preparation of bioabsorbable polymer scaffolds of this invention are, without limitation, polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers that can be used for the carrier/particle-forming of this invention include, again without limitation, naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

Further non-limiting examples of biocompatible biodegradable polymers that may be suitable as carriers herein include, without limitation, polycaprolactone, poly(L-lactide), poly(D,L-lactide), poly(D,L-lactide-co-PEG) block copolymers, poly(D,L-lactide-co-trimethylene carbonate), poly(lactide-co-glycolide), polydioxanone (PDS), polyorthoester, polyanhydride, poly(glycolic acid-co-trimethylene carbonate), polyphosphoester, polyphosphoester urethane, poly(amino acids), polycyanoacrylates, poly (trimethylene carbonate), poly(iminocarbonate), polycarbonates, polyurethanes, polyalkylene oxalates, polyphosphazenes, PHA-PEG, and combinations thereof. The PHA may include poly(α-hydroxyacids), poly(β-hydroxyacid) such as poly(3-hydroxybutyrate) (PHB), poly(3-hydroxybutyrate-co-valerate) (PHBV), poly(3-hydroxyproprionate) (PHP), poly(3-hydroxyhexanoate) (PHH), or poly(4-hydroxyacid) such as poly poly(4-hydroxybutyrate), poly(4-hydroxyvalerate), poly(4-hydroxyhexanoate), poly(hydroxyvalerate), poly(tyrosine carbonates), poly(tyrosine arylates), poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(etheresters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline containing polymer, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, methacrylate polymers containing 2-methacryloyloxyethyl-phosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, elastin protein mimetics, or combinations thereof.

Therapeutic Agents

Any agents that are suitable for treating a kidney cancer and/or an inflammatory disorder of the kidney can be used as therapeutic agents in the present invention.

Examples of therapeutic agents that may be suitable for use in the method of this invention depending, of course, on the specific disease being treated, include, without limitation, anti-restenosis, pro- or anti-proliferative, anti-inflammatory, anti-neoplastic, antimitotic, anti-platelet, anticoagulant, anti-fibrin, antithrombin, cytostatic, antibiotic, anti-enzymatic, anti-metabolic, angiogenic, cytoprotective, angiotensin converting enzyme (ACE) inhibiting, angiotensin II receptor antagonizing and/or cardioprotective agents.

Examples of anti-proliferative agents include, without limitation, actinomycins, taxol, docetaxel, paclitaxel, rapamycin, 40-O-(3-hydroxy)propyl-rapamycin, 40-O-[2-(2-hydroxy)ethoxy]ethyl-rapamycin, or 40-O-tetrazole-rapamycin, 40-epi-(N-1-tetrazolyl)-rapamycin, everolimus, Biolimus A9 (Biosensors International, Singapore), deforolimus, AP23572 (Ariad Pharmaceuticals) and perfenidone.

Examples of antineoplastics and antimitotics include, without limitation, paclitaxel, docetaxel, methotrexate, azathioprine, vincristine, vinblastine, fluorouracil, doxorubicin hydrochloride and mitomycin.

The anti-inflammatory agent can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Examples of anti-platelet, anticoagulant, antifibrin, and antithrombin agents include, without limitation, heparin, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä, calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic and 4-amino-2,2,6,6-tetramethylpiperidine-1-oxyl (4-amino-TEMPO).

Examples of cytostatic or antiproliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil ($\omega$-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Examples of ACE inhibitors include, without limitation, quinapril, perindopril, ramipril, captopril, benazepril, trandolapril, fosinopril, lisinopril, moexipril and enalapril.

Examples of angiogensin II receptor antagonists include, without limitation, irbesartan and losartan.

Other therapeutic agents that may find beneficial use herein include, again without limitation, alpha-interferon, genetically engineered endothelial cells, dexamethasone, antisense molecules which bind to complementary DNA to inhibit transcription, and ribozymes, antibodies, receptor ligands such as the nuclear receptor ligands estradiol and the retinoids, thiazolidinediones (glitazones), enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy, antiviral agents and diuretics.

Presently preferred therapeutic agents are halofuginone, ruboxistaurin, sirolimus, everolimus, zotarolimus, temsirolimus, pimecrolimus and biolimus. In particular, but without limitation, these agents are useful for the treatment of renal diseases.

These agents can also have anti-proliferative and/or anti-inflammatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax a (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable.

Examples of generally biocompatible cations include, without limitation, sodium (Na+), potassium (K+), calcium (Ca+), magnesium (Mg++), iron (Fe+++), ammonium (NH4+) and organic ammoniums formed by protonation of a amine nitrogen of a therapeutic agent. Others are well-known to those skilled in the art and are within the scope of this invention. A presently preferred cation is that arising from the protonation of the piperidine nitrogen of halofuginone:

It is presently preferred that anionic counterions to the above cations such as, without limitation, X— above, be hydrophobic. One of the advantages of using such anions is that the resulting salt may be solvent soluble, a desirable characteristic for the formation of bioabsorbable polymer scaffolds of this invention. Examples of generally biocompatible hydrophobic anions include, without limitation, acetate, propionate, butyrate, valerate, caproate, caprylate, caprate, laurate, myristate, palmate, stearate, palmitolate, oleate, linolate, arachidate, gadoleate, vaccinate, lactate, glycolate, salicylate, desamionphenylalanine, desaminoserine, desaminothreonine, ε-hydroxycaproate, 3-hydroxybutylrate, 4-hydroxybutyrate, 3-hydroxyvalerate, anions of fatty acids, anion of organic phosphates and anions of organic sulfates.

delivering a therapeutically effective amount of the therapeutic agent from the bioabsorbable polymer scaffold in the lumen of the blood vessel with direct access to the kidney to the diseased kidney over an extended period of time, wherein the bioabsorbable polymer scaffold eventually completely absorbs away, and wherein the kidney-related disease is a kidney cancer.

2. The method of claim 1, wherein the bioabsorbable polymer scaffold is a stent.

3. The method of claim 1, wherein the extended period of time is at least 9 months, 12 months, 18 months, 24 months, or 36 months.

4. The method of claim 1, wherein the therapeutic agent is selected from the group consisting of everolimus, halofuginone, ruboxistaurin, sirolimus, zotarolimus, temsirolimus, pimecrolimus and biolimus.

5. The method of claim 4, wherein the therapeutic agent is everolimus.

6. The method of claim 1, wherein the bioabsorbable polymer scaffold comprises a bioabsorbable polymer selected from the group consisting of poly(DL-lactide), poly(L-lactide), poly(D-lactide), poly(L-lactide-co-D,L-lactide), polymandelide, polyglycolide, poly(lactide-co-glycolide), poly (D,L-lactide-co-glycolide), poly(L-lactide-co-glycolide), poly(ester amide), poly(ortho esters), poly(glycolic acid-co-trimethylene carbonate), poly(D,L-lactide-co-trimethylene carbonate), poly(trimethylene carbonate), poly(lactide-co-

---

---

What is claimed is:

1. A method of treating a kidney-related disease in a human patient comprising:

deploying a bioabsorbable polymer scaffold in the lumen of a blood vessel with direct access to a kidney in a diseased condition in the patient, wherein:

the bioabsorbable polymer scaffold comprises a polymer substrate and a polymer matrix coated upon the polymer substrate, both comprising a therapeutic agent; and caprolactone), poly(glycolide-co-caprolactone), poly(tyrosine ester), polyanhydride, derivatives thereof, and a combination thereof.

7. The method of claim 6, wherein the polymer matrix comprises poly(DL-lactide).

8. The method of claim 7, wherein the therapeutic agent is everolimus.

9. The method of claim 8, wherein the ratio of poly(DL-lactide) to everolimus in the polymer matrix is about 1:1.

10. The method of claim 7, wherein the polymer substrate comprises poly(L-lactide).

11. The method of claim 1, wherein the bioabsorbable polymer scaffold maintains a radial strength of at least 200 mmHg for about 3-6 months.

12. The method of claim 1, wherein, prior to deployment, the bioabsorbable polymer scaffold is constrained at a reduced diameter by a sheath and is deployed by removing the sheath and allowing the scaffold to self-expand to the increased diameter.

13. The method of claim 1, wherein, prior to deployment, the scaffold is constrained at a reduced diameter around a balloon and is deployed by expanding the balloon which expands the scaffold to the increased diameter.

14. The method of claim 1, further comprising implanting an additional bioabsorbable scaffold at the site of deployment of the scaffold after it has partially or completely absorbed, wherein the additional scaffold is deployed at a greater diameter than the absorbed scaffold to accommodate for treatment of the diseased kidney.

15. The method of claim 1, wherein the extended period of time is at least 3 months.

16. The method of claim 1, wherein the extended period of time is at least 6 months.

17. A method of treating a kidney-related disease in a human patient comprising:
    deploying a bioabsorbable polymer scaffold into the lumen of a blood vessel with direct access to a kidney in a diseased condition in the patient, wherein:
        the bioabsorbable polymer scaffold comprises a polymer substrate comprising a first therapeutic agent and a polymer matrix coated upon the polymer substrate comprising a second therapeutic agent, wherein the first and second therapeutic agents are different; and
    delivering a therapeutically effective amount of the first and second therapeutic agents from the bioabsorbable polymer scaffold in the lumen of the blood vessel with direct access to the kidney to the diseased kidney over an extended period of time, wherein:
    the bioabsorbable polymer scaffold eventually completely absorbs away, wherein the kidney-related disease is a kidney cancer.

18. The method of claim 17, wherein the extended period of time for the first and second therapeutic agents may be the same or different.

19. The method of claim 17, wherein the extended period of time for the first and the second therapeutic agent is independently at least 9 months, 12 months, 18 months, 24 months, or 36 months.

20. The method of claim 17, wherein the bioabsorbable polymer scaffold is a stent.

21. The method of claim 17, wherein the bioabsorbable polymer scaffold comprises a bioabsorbable polymer selected from the group consisting of poly(DL-lactide), poly(L-lactide), poly(D-lactide), poly(L-lactide-co-D,L-lactide), polymandelide, polyglycolide, poly(lactide-co-glycolide), poly(D,L-lactide-co-glycolide), poly(L-lactide-co-glycolide), poly(ester amide), poly(ortho esters), poly(glycolic acid-co-trimethylene carbonate), poly(D,L-lactide-co-trimethylene carbonate), poly(trimethylene carbonate), poly(lactide-co-caprolactone), poly(glycolide-co-caprolactone), poly(tyrosine ester), polyanhydride, derivatives thereof, and a combination thereof.

22. The method of claim 17, wherein the polymer matrix comprises poly(DL-lactide) and the second therapeutic agent is everolimus.

23. The method of claim 17, wherein the polymer substrate comprises poly(L-lactide) and the first therapeutic agent is everolimus.

24. The method of claim 17, wherein the first or second therapeutic agent is selected from the group consisting of halofuginone, ruboxistaurin, sirolimus, everolimus, zotarolimus, temsirolimus, pimecrolimus and biolimus.

25. The method of claim 24, wherein the first or second therapeutic agents are everolimus.

26. The method of claim 17, wherein the bioabsorbable polymer scaffold maintains a radial strength of at least 200 mmHg for at least 6 months.

27. The method of claim 17, wherein, prior to deployment, the bioabsorbable polymer scaffold is constrained at a reduced diameter by a sheath and is deployed by removing the sheath and allowing the scaffold to self-expand to the increased diameter.

28. The method of claim 17, wherein, prior to deployment, the scaffold is constrained at a reduced diameter around a balloon and is deployed by expanding the balloon which expands the scaffold to the increased diameter.

29. The method of claim 17, further comprising implanting an additional bioabsorbable scaffold at the site of deployment of the scaffold after it has partially or completely absorbed, wherein the additional scaffold is deployed at a greater diameter than the absorbed scaffold to accommodate for treatment of the diseased kidney.

30. The method of claim 17, wherein the extended period of time for the first and the second therapeutic agent is independently at least 3 months.

31. The method of claim 17, wherein the extended period of time for the first and the second therapeutic agent is independently at least 6 months.

* * * * *

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Active fragment of osteopontin

<400> SEQUENCE: 1

Asp Val Asp Val Pro Asp Gly Asp Ser Leu Ala Trp Gly
1               5                   10

<210> SEQ ID NO 2
<211> LENGTH: 69
<212> TYPE: DNA
<213> ORGANISM: Artificial Sequence
<220> FEATURE:
<223> OTHER INFORMATION: Primer

<400> SEQUENCE: 2
tagtgcggcc gcttagcatg ctccgccatg gtgatggtga tgatgcgcac gtttgatttc      60
cagtttggt                                                              69
```